United States Patent
Ohashi et al.

(10) Patent No.: US 6,589,796 B1
(45) Date of Patent: Jul. 8, 2003

(54) METHOD FOR MEASURING IODINE AND REACTION INSTRUMENT FOR SPECIMEN PRETREATMENT

(75) Inventors: Toshinori Ohashi, Ibaraki (JP); Mituo Yamaki, Ibaraki (JP); Minoru Irie, Tokyo (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/555,681

(22) PCT Filed: Dec. 1, 1998

(86) PCT No.: PCT/JP98/05408

§ 371 (c)(1),
(2), (4) Date: Jun. 2, 2000

(87) PCT Pub. No.: WO99/28741

PCT Pub. Date: Jun. 10, 1999

(30) Foreign Application Priority Data

Dec. 2, 1997 (JP) ............................................. 9-332237

(51) Int. Cl.[7] ................... G01N 33/48; G01N 1/44; G01N 33/487; G01N 33/493
(52) U.S. Cl. ................... 436/124; 436/125; 436/126; 436/155; 436/159; 436/166; 436/175
(58) Field of Search ................... 422/100, 102, 422/104; 436/124–126, 155, 159, 164, 166, 175, 183

(56) References Cited

U.S. PATENT DOCUMENTS

| | | | |
|---|---|---|---|
| 3,276,847 A | * 10/1966 | Duff et al. | |
| 4,593,728 A | * 6/1986 | Whitehead et al. | 422/100 X |
| 4,735,778 A | * 4/1988 | Maruyama et al. | 422/102 |
| 4,882,127 A | * 11/1989 | Rosenthal et al. | 422/50 |
| 4,919,811 A | 4/1990 | Davis | 210/500.36 |
| 4,980,293 A | * 12/1990 | Jeffs | 422/102 X |
| 5,141,719 A | * 8/1992 | Fernwood et al. | 422/101 |
| 5,219,528 A | * 6/1993 | Clark | 422/101 |
| 5,319,436 A | * 6/1994 | Manns et al. | 356/246 |
| 5,342,581 A | * 8/1994 | Sanadi | 422/101 |
| 5,540,891 A | 7/1996 | Portmann et al. | 422/102 |
| 5,545,528 A | * 8/1996 | Mitsuhashi et al. | 435/6 |
| 5,604,130 A | * 2/1997 | Warner et al. | 422/102 X |
| 5,665,558 A | * 9/1997 | Frame et al. | 422/102 X |
| 5,792,426 A | 8/1998 | Portmann et al. | 422/102 |
| 5,842,573 A | * 12/1998 | Halvorsen | 206/569 |

FOREIGN PATENT DOCUMENTS

| | | | |
|---|---|---|---|
| EP | 542422 | * | 5/1993 |
| JP | 62-50729 | | 3/1987 |
| JP | 2-5067 | | 1/1990 |
| JP | 2-35360 | * | 2/1990 |
| JP | 7-37332 | | 7/1995 |

OTHER PUBLICATIONS

G. Palumbo et al, Anal. Biochem. 1982, 123, 183–189.
A. A. Olkowski et al, Int. J. Vitam. Nutr. Res. 1992, 62, 34–42.
J. T. Dunn et al, Thyroid 1993, 3, 119–123.
A. A. Olkowski et al, Chem. Abstr. 1993, 119, abstract 134668h.*
M. Ogura et al, Anal. Biochem. 1994, 218, 458–459.*

(List continued on next page.)

Primary Examiner—Arlen Soderquist
(74) Attorney, Agent, or Firm—Foley & Lardner

(57) ABSTRACT

A iodine-measuring method for determining or detecting iodine concentration in a specimen, comprising a specimen-pretreating step of thermally digesting a specimen together with an oxidizing agent, and a subsequent reaction-measuring step of reacting the resultant with an arsenious acid reagent solution and an ammonium cerium sulfate reagent solution and measuring absorbance in the reaction solution, characterized in that the specimen-pretreating step is performed by heating and cooling treatment under an airtight condition.

7 Claims, 4 Drawing Sheets

OTHER PUBLICATIONS

S. Coverly Chem. Abstr. 1996, 124, abstract 311747j.*
Z. Yaping et al, Clin. chem. 1996, 42, 2021–2027.*
S. L. May et al, Am. J. Clin. Nutr. 1997, 65, 1441–1445.*
J. Fischi Clin. Chim. Acta 1956, 1, 462–469.*
G. W. F. H. B. Pauwels et al, Anal. Chim. Acta 1962, 26, 532–540.*
G. M. Widdowson et al, Clin. Chim. Acta 1963, 8, 636–639.*
J. Benotti et al, Clin. Chem. 1965, 11, 932–936.*
E. T. Backer et al, Clin. Chim. Acta 1967, 15, 77–85.*
R. O'Kennedy et al, Anal. Biochem. 1989, 179, 138–144.*
J. P. Schofield et al, Nucleic Acids Res. 1989, 17, 9498.*
W. May et al, Clin. Chem. 1990, 36, 865–869.*
Pino, S., Fang Shih–Lieh and Braverman, E. (1996) Ammonium persulfate: a safe alternative oxidizing reagent for measuring urinary iodine Clinical Chemistry 42:239–243.

Tsuda, K., Namba H,. Nomura, T., Yokoyama, N., Yamashita, S., Izumi, M. and Nagataki. (1995). Automated Measurement of urinary iodine with use of ultraviolet irradiation. Clin. Chem 41:581–585.

Sanz, M.C., Brechbühler and Green, I.J. (1956). The ultra-micro–determination of total and protein–bound iodine. Clinica Chimica Acta 1:570–576.

Zak, B., Willard, H.H., Myers, G.B., Boyle, A.J. (1952). Chloric acid method for determination of protein–bound iodine. Analytical Chemistry 24:1345–1348.

International council for control of iodine deficiency disorders. (1993) Method for measuring iodine in urine.

Journal of Analytical Atomic Spectrometry vol. 11, (1996), p731–734, V. Poluzzi et al. Chloric acid method.

* cited by examiner

METHOD FOR MEASURING IODINE AND REACTION INSTRUMENT FOR SPECIMEN PRETREATMENT

TECHNICAL FIELD

The present invention relates to a method for measuring iodine, a specimen-pretreating reaction tool, and an airtight tool for the specimen-pretreating reaction tool.

BACKGROUND ART

Iodine is an indispensable trace element that becomes a raw material of the thyroid hormone for promoting metabolism of a living body, and the iodine content in the body is 15–20 mg for a healthy adult. The weight of the human thyroid hormone in any adult is about 20 g, and the thyroid gland causes iodine in blood to be selectively concentrated and generates the thyroid hormone. The intake, per day, necessary for any living body is said to be 100–150 μg. If this iodine lacks and this state is left as it is, goiter is generated and further the function of the thyroid gland deteriorates. Particularly, newborn infants come to undergo a drop in intelligence, hypoplasia, neurological symptoms and the like. Pregnant women's shortage of iodine is said to result in stillbirths and an increase in the death rate of newborn infants.

The number of people who live in regions where there is a risk of the shortage of iodine is said to be about 16 hundred million. Such people are concentrated in developing countries. It is said that this is because in inland and mountainous regions or regions where floods arise frequently or the amount of precipitation is much, by the outflow of iodine from soil the iodine content in plants that grow therein becomes insufficient so that people and animals who/that live therein have a short intake of iodine, thereby suffering from iodine deficiency disorder. For a preventive measure for the disorder, it is said that effective is a relatively simple method, such as supplementation of iodine, for example, an intake of iodized salt. In reality, in USA, European nations and the like, the measure based on this method produces an advantageous effect in iodine-shortage regions.

In such a situation, a target of the eradication of iodine deficiency disorder was adopted in the world summit for children by the United Nations in 1990, and the eradication is listed as one of important themes of International Council for Control of Iodine Deficiency Disorders (ICCIDD), UNICEF and the World Health Organization (WHO), or is listed as a state measure of a great number of nations. For this, it is important that the actual conditions of iodine deficiency disorder are precisely grasped, the disorder is diagnosed and treated, and the actual conditions are periodically being monitoring.

It is said that iodine deficiency disorder can be diagnosed by measuring iodine in urine since the intake of iodine and the excretion amount of iodine into urine have a good correlation. The normal value of iodine in urine, which is an index for this diagnosis, is said to be 100 μg/L or more.

As a method for measuring iodine, E. B. Sandell et al. reports calorimetric determination using the property that iodide ion functions as a catalyst for increasing the rate of a redox reaction represented by the chemical reaction equation (I) (and abbreviated to Sandell-Kolthoff reaction hereinafter. E. B. Sandell and Kolthoff, Mikrochemica Acta, vol. 1, P9–25(1937)).

$$2Ce^{4+}+As^{3+} \rightarrow 2Ce^{3+}+As^{5+} \qquad (I)$$

That is, this is a sensitive measuring method using the fact that iodine functions, as shown by the chemical reaction equations (II) and (III), as a catalyst for a reaction that by adding an arsenious acid reagent solution and an ammonium cerium sulfate reagent solution as reagents to iodide ion in a specimen, yellow ammonium cerium sulfate (quadrivalent ion) is reduced to produce colorless trivalent cerium ion.

$$2Ce^{4+}+2I^- \rightarrow 2Ce^{3+}+I_2 \qquad (II)$$

$$I_2+As^{3+} \rightarrow 2I^-+As^{5+} \qquad (III)$$

In measurement of a specimen such as urine, however, the specimen contains a large amount of interference materials having an effect on this redox reaction, such as ion of ascorbic acid and ion of thiocyanic acid. Thus, the specimen cannot be applied, as it is, to this reaction. Actual measurements require pretreatment such as removal of the interference materials in the specimen. As the pretreatment, the following methods are suggested: a method of heating a specimen intensely and incinerate it (M. C. Sanz et al., Clinica Chemica Acta, 1, 570–576, 1956), a wet incinerating method of adding an oxidizing agent such as perchloric acid or chloric acid, and heating the resultant to oxidize interference materials (Zak et al., Anal. Chem., 24(8), 1345–1348, 1952), and a method of separating interference materials by dialysis, chromatography or the like (WO96/27794). Among these pretreating methods, the wet incinerating method according to Zak et al. is used as a simplest method. As a mildest and standard wet incinerating method, there is suggested and performed a method of adding 250 μl of a specimen of urine and 750 μl of a chloric acid reagent solution into a glass test tube 10 cm in length and 13 mm in inner diameter in a locally-exhausting provision, heating the test tube at 110–115° C. for 1 hour with a sand bath or an aluminum block under an open condition, cooling the tube, adding 3.5 ml of an arsenious acid reagent solution that is acidified with sulfuric acid into the tube to conduct reduction reaction for 15 minutes, adding 350 μl of an ammonium cerium sulfate reagent solution into the tube, and subjecting this solution to calorimetric determination at 405 nm after the reaction for a certain time (Manual of measurement of iodine in urine, edited by International Council for Control of Iodine Deficiency Disorders, 1993).

However, it is required that a vessel used in the above-mentioned chloric acid-using pretreatment of a urine specimen is made of a raw material which can endure even if the raw material is heated together with such a strong oxidizing agent as chloric acid, and it is also required that, from the vessel, materials which interfere in the Sandell-Kolthoff reaction following the pretreatment do not flow out. Therefore, no vessel made of a polymer material has been used for the chloric acid-using pretreatment of specimens. Moreover, vapor discharged in the pretreatment step is vapor containing chlorine having an irritant smell, or the like. Thus, it is necessary that the pretreatment is performed in a locally-exhausting provision having an exhaust device. For this reason, there is being performed a method of using a glass test tube resisting both heat and any oxidizing agent as a vessel in the locally-exhausting provision having the exhaust device and further heating it together with an oxidizing agent in an open state from the viewpoint of a problem about strength. Besides, in the method of heat-treating a specimen in the glass vessel in an open state, in order to decrease a change in the amount of the solution therein by evaporation and scattering of the specimen, reagent solutions and the like, it is necessary to use a long test tube having a volume scale of 1 ml or more.

The long test tube having a volume scale of 1 ml or more is used; therefore, in order to treat a great number of specimens at the same time, it is necessary to use a wider treating space and a large-scaled heating device. Furthermore, in the chloric acid-using pretreatment of a specimen, in order to discharge harmful vapor originating from chloric acid, which is generated upon heating the specimen together with chloric acid, it is necessary to use the locally-exhausting provision. In the measurement, the color fading reaction (Sandell-Kolthoff reaction) after adding the arsenious acid reagent solution and the ammonium cerium sulfate reagent solution as reagents to iodide ion in a specimen is a relatively speedy and sensitive reaction. For this reason, in measuring an absorbance when a given time passes after the start of the color fading reaction, strictness of measuring-time is required. Therefore, in the measurement wherein specimens are transferred from test tubes to cells for absorbance-measurement one tube by one tube, capability of treating specimens is restrictive, and a measuring method for treating a great number of specimens is demanded. As an automatic device for treating a great number of specimens of urine, using Sandell-Kolthoff reaction, there is an auto-analyzer made by Technicon Instrument Company, but this device cannot be said to be a device having simplicity for operation and capability of being transported.

Furthermore, recently, Pino et al. have reported that a pretreating method wherein ammonium persulfate is used as an oxidizing agent without use of chloric acid (Clinical Chemistry, 42(2), 239–243, 1996) is a safe method. However, this pretreating method is also a method of using a glass test tube in an open state to perform heating, and has the same problem as the method using chloric acid. Thus, it is difficult that a great number of specimens are treated. In this pretreating method, the safety of gas generated upon heating has not yet been verified.

In methods of measuring iodine, toxic substances or deleterious substances such as arsenic, cerium and sulfuric acid are used as reagents. Thus, if a great number of specimens are measured, a large amount of harmful waste, which results in an environmental problem, comes to be produced. Actually, according to the above-mentioned Manual of measurement of iodine in urine, 4.85 ml of a waste solution containing arsenic are produced for each specimen.

In many cases, regions where measurement of iodine is necessary are regions that are distant from cities. Thus, there are strongly demanded a measuring method that can be safely performed and a measuring tool and a measuring device that have excellent capability of being transported.

Recently, Tsuda et al. have reported an automatic device for performing pretreatment by oxidization through both potassium persulfate and irradiation of ultraviolet rays (K. Tsuda et al., Clinical Chemistry, 41(4), 581–585 (1995)), and Poluzzi et al. have also reported and suggested a measuring method using ICP/MS or HPLC (V. Poluzzi et al., J. of Anal. Anal. Atomic Spectrometry, 11(9), 731–734 (1996)). However, it is difficult to accept introduction of these devices that are expensive and lack the capability of being transported.

DISCLOSURE OF THE INVENTION

The invention provides a method for measuring iodine which does not require any special provision such as a locally-exhausting provision in pretreatment and which makes it possible to pretreat a specimen safely and obtain measured values with good reproducibility by suppressing scattering of harmful vapor and a change in the solution amount of a reaction solution.

The invention provides a method for measuring iodine which makes it possible to pretreat a specimen with safety and high reliability since there do not arise troubles such as damage of any vessel upon heating treatment.

The invention provides a method for measuring iodine which does not require any special provision such as a locally-exhausting provision in pretreatment and which makes it possible to pretreat a specimen with safety and high reliability and obtain measured values with good reproducibility by suppressing scattering of harmful vapor and a change in the solution amount of a reaction solution and by no occurrence of troubles such as damage of any vessel.

The invention provides a method for measuring iodine which makes it possible to pretreat a great number of specimens promptly and easily and is suitable for measuring a great number of specimens.

The invention provides a method for measuring iodine which makes it possible to pretreat a specimen with safety and high reliability by no occurrence of troubles such as damage of any vessel upon heating treatment and no outflow of such materials that have an effect on measured values.

The invention provides a method for measuring iodine which makes it possible to obtain a low-priced and highly reliable reaction tool and pretreat safely a specimen without troubles such as damage of any vessel upon heating treatment nor outflow of such materials that have an effect on measured values.

The invention provides a specimen-pretreating reaction tool that is suitable for iodine measurement which makes it possible to pretreat safely a great number of specimens without troubles such as damage of any vessel upon heating treatment nor outflow of such materials that have an effect on measured values.

The invention provides an airtight tool, for the specimen—pretreating reaction tool, which does not require any special provisions such as a locally—exhausting provision in pretreatment of specimens for measuring iodine, does not impose any limitations on places where specimens are treated, and can suppress evaporation of harmful vapor and the generation amount of harmful waste, and which is suitable for iodine measurement that makes it possible to treat a great number of specimens easily.

(1) The present invention relates to a iodine—measuring method for determining or detecting iodine concentration in a specimen, comprising a specimen—pretreating step of thermally digesting a specimen together with an oxidizing agent, and a subsequent reaction—measuring step of reacting the resultant with an arsenious acid reagent solution and an ammonium cerium sulfate reagent solution and measuring absorbance in the reaction solution, characterized in that the specimen—pretreating step is performed by heating and cooling treatment under an airtight condition.

(2) The present invention relates to a iodine-measuring method for determining or detecting iodine concentration in a specimen, comprising a specimen-pretreating step of thermally digesting a specimen together with an oxidizing agent, and a subsequent reaction-measuring step of reacting the resultant with an arsenious acid reagent solution and an ammonium cerium sulfate reagent solution and measuring absorbance in the reaction solution, characterized in that the specimen-pretreating step is performed by using a reaction tool made of a heat-resistant organic material.

(3) The present invention relates to a iodine-measuring method for determining or detecting iodine concentration in a specimen, comprising a specimen-pretreating step of thermally digesting a specimen together with an oxidizing agent, and a subsequent reaction-measuring step of reacting the resultant with an arsenious acid reagent solution and an ammonium cerium sulfate reagent solution and measuring absorbance in the reaction solution, characterized in that the specimen-pretreating step is performed by heating and cooling treatment under an airtight condition, using a reaction tool made of a heat-resistant organic material.

(4) The present invention relates to the iodine-measuring method according to the above-mentioned (2) or (3), wherein the reaction tool made of the heat-resistant organic material is a tool having plural reaction areas.

(5) The present invention relates to the iodine-measuring method according to any one of the above-mentioned (2)–(4), wherein the heat-resistant organic material is a polypropylene resin, a polycarbonate resin, a polysulfone resin, a polyethersulfone resin, a Teflon resin, or a polymethylpentene resin.

(6) The present invention relates to the iodine-measuring method according to any one of the above-mentioned (2)–(5), wherein the reaction tool is a microtiter plate.

(7) The present invention relates to a specimen-pretreating reaction tool for measuring iodine, comprising at least one heat-resistant organic material selected from the group consisting of a polypropylene resin, a polycarbonate resin, a polysulfone resin, a polyethersulfone resin and a polymethylpentene resin, and having plural reaction areas capable of thermally digesting plural specimens together with an oxidizing agent.

(8) The present invention relates to an airtight tool composed of the specimen-pretreating reaction tool for measuring iodine recited in the above-mentioned (7), and two, upper and lower fixing supporters which can cover plural reaction areas of this reaction tool with a spacer sandwiched and fixed from upper and lower sides, and fixing assistance members capable of applying pressure to these fixing supporters so that the reaction areas of the reaction tool can be made airtight by aid of spacer.

The following will describe a reaction tool used in the step of pretreating a specimen in the method for measuring iodine according to the present invention.

It is necessary that this reaction tool withstands treatment of thermally digesting a specimen together with an oxidizing agent. In order to suppress the generation of harmful vapor which is generated by heating in the specimen-pretreating step of heating the specimen together with the oxidizing agent, such as chlorine gas originating from chloric acid, and minimize the reproducibility (dispersion) between measured values by a change in solution amount, it is also necessary that this tool withstands airtight conditions.

The above-mentioned reaction tool preferably has plural reaction areas. Examples of such a reaction tool include a tool wherein reaction plural areas, each of which is composed of a vessel such as a test tube or a test tube for centrifugation, are lined up and connected to each other, and a tool wherein plural reaction areas, each of which is composed of a well-form or columnar-form concave portion dug made in a single plate, are lined up.

The shape of each of the reaction areas may be a U-shaped form, or a flat bottom form, as is seen about test tubes, or may be a V-shaped form, as is seen about test tubes for centrifugation.

The volume of each of the reaction areas is preferably 200–1000 $\mu$l. It is more preferably 300–500 $\mu$l, and still more preferably 300–350 $\mu$l. If the volume of each of the reaction areas is more than 1000 $\mu$l, a useless space increases in volume, following the enlargement of the size of the vessel. Thus, the operation of treating a great number of specimens trends to become difficult. If it is less than 300 $\mu$l, there are required fine operation of fractional pour of specimens and reagent solutions and strictness of any operation so as to trend to promote a drop in fractional pour precision and a risk of erroneous operation in treatment of a great number of specimens.

Moreover, an opening of each of the reaction areas preferably has a shape or structure that can ensure airtightness by aid of a spacer for covering the reaction area to attain an airtight state. Examples of the spacer include lid-form, sheet-form and plate-form spacers. When the lid-form spacer is used, the surface shape or structure of the opening of each of the reaction areas is preferably made complementary to the lid in a concave or convex form. When the sheet-form or plate-form spacer that is flat is used, the surface shape in the vicinity of the opening of each of the reaction areas is preferably made flat. Furthermore, in order to ensure airtightness, it is preferable to make larger the area where the spacer contacts the opening of each of the reaction areas.

The raw material of the reaction tool is preferably a heat-resistant organic material. Among such heat-resistant organic materials, preferable are organic materials that are excellent in heat-resistance and chemical resistance against oxidizing agents, have a high physical strength and can easily be molded. Preferably, by heating the organic material together with an oxidizing agent, such materials that interfere in the reaction following pretreatment do not flow out from the vessel. Examples of such raw materials include polypropylene, polycarbonate, polysulfone, polyethersulfone, Teflon and polymethylpentene resins.

A specific example of the reaction tool is a microtiter plate. In general, the microtiter plate has an integration-type form in which 96 wells (reaction areas) about 8 mm in diameter and about 8 mm in depth are arranged in a single plate so as to make 8 rows in a lengthwise direction and 12 rows in a lateral direction. However, the microtiter plate that can be used in the iodine-measuring method of the present invention is not limited to the microtiter plate having the above-mentioned number of the wells, diameter and depth and the like. For example, the diameter may be made smaller, or the depth may be made larger. Moreover, there may be used a division-type microtiter plate in which arbitrary number of wells are combined, using each unit of 8 lengthwise rows or 12 lateral rows, so that 96 wells can be divided.

In the present invention, the reaction tool is not limited to the above-mentioned microtiter plate. An example thereof is an 8-series tube for PCR (Polymerase Chain Reaction) made of polypropylene. In the tube, 8 reaction areas, each of which has a diameter of about 6 mm and a depth of about 20 mm and is in the form of a test tube for centrifugation, are linearly connected to each other (imported and sold by Assist Co., Ltd.). This 8-series tube can also be used. The number of the reaction areas in the reaction tool made of such a heat-resistant organic material is not limited, and can be appropriately selected in accordance with the number of specimens to be treated, the frequency of treatment and the like.

In the iodine-measuring method of the present invention, the reaction areas in the reaction tool are preferably made into an airtight state by means of the spacer in the specimen-pretreating step of thermally digesting a specimen together with an oxidizing agent. It is necessary that the spacer can withstand the pretreatment of the specimen.

The spacer is preferably made of a material that has no permeability of gas, and has both of chemical resistance against oxidizing agents and heat-resistance that does not cause deformation at a treating temperature (for example, 120° C.) Examples thereof include polypropylene, polycarbonate, polysulfone, polyethersulfone, Teflon, and polymethylpentene resins; and silicone, butyl and chlorobutyl rubbers. The spacer may be preferably made of a sheet-form or plate-form material having elasticity. Examples of the material of the sheet-form or plate-form spacer include silicone, butyl and chlorobutyl rubbers. As a film for preventing these covers from deteriorating, it is preferable to coat the covers with a heat-resistant film such as a polypropylene film, a polychlorovinylidene film, a fluoroethylene film, or the like.

The surface of the opening of each of the reaction areas and the spacer are manually made flat, or are made or work-molded into complementary shapes or structures having convex and concave portions, in order to keep close adhesion and airtightness.

In the case that the number of specimens to be treated is small, the spacer preferably has a lid shape from the viewpoint of economy. In the case that a great number of specimens are treated, the spacer preferably has a cover shape from the viewpoint of easiness of the operation thereof and efficiency of the multi-specimen treatment.

The airtight tool for the pretreating reaction tool is preferably made of a heat-resistant material that is not deformed at a treating temperature (for example, 120° C.) since the airtight tool accommodates the reaction tool and the spacer and attains treatment in a thermostat or a similar constant-temperature heater. A preferable heat-resistant material of a fixing supporter or a fixing assistance member for this may be a metal, a heat-resistant hard resin, or the like. More preferably, the heat-resistant material may be a material made of carbon, or a metal having a good heat conductivity, such as aluminum, copper or stainless steel from the standpoint of efficiency of heating a specimen in the pretreating step and cooling it to room temperature after the heating treatment.

If vapor of the treated solution condenses onto the spacer after the heating, a change in its solution amount arises so as to damage the reproducibility of measurement. Therefore, in such a manner that upon cooling, a lower supporting plate of the fixing supporter is cooled earlier than an upper supporting plate contacting the spacer, it is preferable that the lower supporting plate is forcibly brought into contact with water or a heat-radiating plate, that the upper supporting plate is made thicker than the lower supporting plate, or that the upper supporting plate is made of a raw material that has a lower heat conductivity than that of the lower supporting plate. For example, a raw material having a high heat conductivity, such as aluminum or copper, is preferably used for the lower supporting plate while a raw material having a lower heat conductivity than the lower supporting plate, for example, stainless steel, is preferably used for the upper supporting plate. More preferably, these are combined.

FIGS. 1–3 illustrate an example of the airtight tool, but the airtight tool is not limited to this example.

FIG. 1 illustrates a front view of the example of the airtight tool (in use). FIG. 2 illustrates a plan view thereof (in use). FIG. 3 illustrates a sectional view (in the state that any snap screw as one fixing assistance member is taken off), which is taken on a–a' line of FIG. 2.

The airtight tool comprises an upper supporting plate 2, a lower supporting plate 3, and a fixing assistance members 4 fitted to the lower supporting plate 3, such as snap screws made of aluminum or the like.

A reaction tool 5 such as a microtiter plate is put in a receiving space, which is made by the upper supporting plate 2 and the lower supporting plate 3, in the state that the tool 5 is sandwiched between two spacers 6 and 7 and openings of wells are directed upward. Reaction areas of the reaction tool 5 adhere closely to the spacer 6 and are made into an airtight state by fastening the lower supporting plate 3 and the upper supporting plate 2 from the upper and lower sides by means of the fixing assistance member 4 fitted to the lower supporting plate 3. In FIG. 3, the spacer 7 between the reaction tool 5 and the lower supporting plate 3 may not be used. It is necessary that the spacer 6 between the reaction tool 5 and the upper supporting plate 2 has such a thickness that can ensure the airtightness of the reaction areas of the reaction tool 5.

The following will describe the iodine-measuring method of the present invention.

The iodine-measuring method of the present invention is preferably performed as follows: in a method for determining or detecting iodine concentration in a specimen, comprising a specimen-pretreating step of thermally digesting a specimen together with an oxidizing agent, and a subsequent reaction-measuring step of reacting the resultant with an arsenious acid reagent solution and an ammonium cerium sulfate reagent solution and measuring absorbance in the reaction solution, the specimen-pretreating step is performed by heating and cooling treatment under an airtight condition.

In the pretreatment of a specimen in the iodine-measuring method of the present invention, for example, a definite amount of a iodine standard solution or a definite amount of the specimen such as urine, and a definite amount of an oxidizing agent such as a chloric acid reagent solution are added to each of the reaction areas of the reaction tool. After the addition of the oxidizing agent, the spacer or the airtight tool is used to make the each of the reaction areas airtight. A thermostat or the like is used to heat-treat the reaction tool made airtight at a constant temperature for a definite time. After this heat-treatment, the temperature of the reaction tool is returned to room temperature. By this pretreatment, interference materials upon measurement of the specimen are removed and further iodide ion and iodine are oxidized to iodate ion.

In the iodine-measuring method of the present invention, the specimen may be urine of humans or animals. The specimen may be a iodine standard solution having a known concentration. The specimen is not limited to these. If a solution seems to contain iodine or a specimen can be made up to an aqueous solution, the solution or the specimen is allowable.

In the iodine-measuring method of the present invention, the solution amount of the specimen is preferable within the range of 2–100 $\mu$l, more preferably within the range of 3–80 $\mu$l, and still more preferably within the range of 5–50 $\mu$l. If the solution amount is less than 2 $\mu$l, the sensitivity of the measurement is bad and an accidental error in fractional pour becomes large. Thus, the reproducibility of the measurement trends to deteriorate. If the solution amount is more than 100 $\mu$l, the amounts of pretreating agents for coping with it and reagent solutions of the measurement increase so that quickness of operation and the capability of multi-specimen measuring treatment trend to be damaged.

The solution amount of the added oxidizing agent is preferably 2–10 times that of the specimen. If the solution amount of the added oxidizing agent is less than 2 times that of the specimen, final concentration drops so that the recovery ratio of iodine trends to drop. If the solution amount of the added oxidizing agent is more than 10 times that of the specimen, the reagent becomes fruitless and further the discharge amount of harmful waste, which comes into an environmental problem, increases. Particularly in the case of multi-specimen treatment, they come into problems that cannot be ignored. In this range, the maximum solution amount, which results from summing up the added amounts of the specimen and the oxidizing agent, is preferably 70% or less by volume of the vessel in accordance with the volume of the vessel, and more preferably 20–50% by volume of the vessel. If the maximum solution amount is more than 70% by volume of the vessel, stirring becomes difficult or it is feared that the treated solution cannot be recovered by adhesion of the treated solution to the spacer.

The oxidizing agent may be chloric acid, ammonium persulfate or the like. In the case that chloric acid is used, the final concentration thereof in the pretreating step is preferably 10–30 (W/V)%. If it is less than 10 (W/V)%, removal of interference materials from a specimen is insufficient so that the recovery ratio of iodine falls and such recoveries are largely scattered in accordance with the particular specimens. Thus, a good reproducibility of measured values trend not to be obtained. If the final concentration of chloric acid is more than 30 (W/V)%, the chloric acid reagent solution becomes fruitless and further a large amount of harmful waste is produced. If it is 40% or more, there arises such a problem that self-decomposition is caused (Kagaku Dai-Ziten, the item of chloric acid). In the case of using ammonium persulfate, the final concentration thereof is preferably 15–30 (W/V)%. If it is less than 15 (W/V)%, the recovery of iodine from iodine in a specimen becomes insufficient and such recoveries are largely scattered. Thus, a good reproducibility of measured values trends not to be obtained. If it is more than 30 (W/V)%, ammonium persulfate becomes fruitful. Moreover, ammonium persulfate whose concentration is too high trends to block, in a subsequent reaction (Sandell-Kolthoff reaction) based on the addition of an arsenious acid reagent solution and an ammonium cerium sulfate reagent solution. Therefore, the use thereof at a high concentration is not preferred.

In the pretreatment of a specimen, reaction temperature upon thermally digesting the specimen together with the oxidizing agent is preferably 50–40° C., more preferably 80–120° C. and especially preferably 100–110° C. from the viewpoint of the removal of interference materials. If it is below 50° C., the recovery of iodine in the specimen becomes insufficient and such recoveries are largely scattered. Thus, a good reproducibility of measured values trend not to be obtained. If it is over 140° C., no problems arise in the recovery of iodine in the specimen. However, if it exceeds the limit of heat-resistance of the reaction tool made of a heat-resistant organic material, it is feared that the deformation of the reaction areas of the reaction tool makes it impossible to block evaporation of harmful vapor and the scattering of the reagent solution.

Reaction time upon thermally digesting together with the oxidizing agent is preferably 30–120 minutes, and more preferably 45–90 minutes. If it is less than 30 minutes, iodine is insufficiently recovered from iodine in a specimen and such recoveries are largely scattered. Thus, a good reproducibility of measured values trends not to be obtained. If it is more than 120 minutes, the scattering in recoveries and the reproducibility of measured values do not change. However, the capabilities of rapid measurement and multi-specimen treatment are decreased. Within the above-mentioned range, concentration, temperature and time making it possible to oxidize organic materials or the like in the specimen sufficiently and recover iodine can be appropriately selected.

As described above, in the pretreatment of a specimen, the heating reaction is preferably performed under an airtight condition in order to suppress the generation of harmful vapor generated by heating, such as chlorine gas originating from chloric acid, and minimize the reproducibility (scattering) between measured values, following a change in the solution amount by evaporation of the reaction solution. In the pretreatment, the airtight condition is more preferably such an airtight condition that makes it possible to suppress a change in the solution amount within 2% before and after the pretreatment.

In order to attain the airtight condition, it is preferable that the above-mentioned spacer is used. By attaining the airtight condition in this way, the pretreatment of a specimen can be more safely conducted. In the case of an insufficient airtight condition, the pretreatment may be conducted in a locally-exhausting provision.

In order to make the airtight condition based on the spacer more certain, or treat a great number of specimens at the same time, an airtight tool for the above-mentioned reaction tool is preferably used. In the case that the airtight tool for the reaction tool is used, the multi-specimens can be simultaneously treated, without use of a special provision such as a locally-exhausting provision, more safely than in the case that only the spacer is used.

From the viewpoint of the pretreatment-safety for avoiding harmful vapor such as chlorine gas and the shortening of cooling time, it is more preferable that after the pretreatment of a specimen the reaction temperature of the pretreatment is positively returned to room temperature or lower by cooling or the like. In view of safety, it is necessary not to open the spacer or the airtight tool for the reaction tool until the reaction temperature of the pretreatment is returned to room temperature. By this cooling treatment, harmful gas is hardly emitted even if the airtight state is cancelled.

In the step subsequent to the above-mentioned step of pretreating a specimen, an arsenious acid reagent solution is first added to the treatment solution subjected to the pretreatment and then a yellow ammonium cerium sulfate reagent solution is added thereto so as to perform a reaction in which its color is faded (Sandell-Kolthoff reaction). For example, the temperature of the pretreated solution is returned to room temperature and subsequently a definite amount of this solution is transferred to a microtiter plate made of polystyrene. A definite amount of the arsenious acid reagent solution is added thereto. In this way, iodate ion is reduced to become iodide ion.

Next, the ammonium cerium sulfate reagent solution, which is a yellow ammonium cerium sulfate solution, is added thereto so as to start a reduction reaction (color-fading reaction) of ammonium cerium sulfate by arsenious acid, using iodine as a catalyst.

Concerning final measurement of absorbance in the present invention, a change in the color fading reaction caused by the addition of the ammonium cerium sulfate reagent solution is measured as a change in absorbance or transmittance. The concentration of iodine in a specimen is determined or detected from the relationship between measured values of the absorbance or transmittance and the amounts of iodine.

The respective reagent solutions may be prepared and used in the following ways, but the compositions thereof are not limited to the following compositions.

The arsenious acid reagent solution may be prepared, for example, by adding and dissolving 10 g of arsenious acid together with 7 g of sodium hydroxide into 250 ml of purified water, adding 32 ml of concentrated sulfuric acid thereto so as to turn the solution into acidity, adding 25 g of sodium chloride thereto, and adding purified water thereto so as to make its volume up to 1 liter. The resultant solution is stored at room temperature in the state that light is blocked off.

The ammonium cerium sulfate reagent solution may be prepared by dissolving 24 g of ammonium cerium sulfate into 3.5 N sulfuric acid to make the resultant solution up to 1 liter. The resultant solution is stored at room temperature in the state that light is blocked off.

In the present invention, in any case other than the case in which a transparent tool (particular, a transparent microplate) is used as the reaction tool used in the pretreatment, it is necessary to transfer a definite amount of the treated solution to a measuring tool having such transparency that any change in absorbance can be measured before or after the addition of the arsenious acid reagent solution (for example, a microplate).

As the measuring tool having such transparency that any change in absorbance can be measured, particularly the microplate, it is allowable to use any plate making it possible to measure absorbance, which is made of, for example, polystyrene. The volume of its wells is preferably 300–500 $\mu$l, more preferably 300–400 $\mu$l, and still more preferably 300–350 $\mu$l. If the volume is over 500 $\mu$l, the size of the vessel becomes large so that a needless space is necessary. Therefore, multi-specimen treatment trends to become difficult. If the volume is below 300 $\mu$l, the size of the vessel becomes fine so that fine actions, such as fractional pour of a specimen and reagent solutions, and strictness of operations are required. Thus, fractional pour precision deteriorates and the risk that erroneous operations in multi-specimen treatment are caused trends to increase.

Concerning the measurement of absorbance in the present invention, a change in the color-fading reaction of the added ammonium cerium sulfate reagent solution is measured as a change in absorbance or transmittance.

The change in absorbance or transmittance is measured after the start of the color-fading reaction of the added ammonium cerium sulfate reagent solution. The measurement of the change in absorbance or transmittance is preferably measured by endpoint assay of measuring a change in the color-fading reaction as absorbance or transmittance at the time when a certain time passes after the start of the reaction, or reaction rate assay of measuring absorbances or transmittance after the start of the reaction, in progress of the reaction, and obtaining a difference therebetween (reaction rate). In the case that they are measured 3 times or more in the progress of the reaction, the reaction rate can be obtained by a calculating method such as the least-squares method.

In these measurements, the absorbance of a single wavelength selected from the range of 400–450 nm, as a measuring wavelength, is preferably measured. Furthermore, in order to decrease a change in measured values between wells of the microtiter plate, based on their stains, injuries or the like, a difference between absorbances of two different wavelengths is preferably measured, one of which is selected from the range of 400–450 nm as a main wavelength, and the other of which is selected from the range of 450–700 nm as a secondary wavelength.

In the case that, after the start of the color-fading reaction by the addition of the ammonium cerium sulfate reagent solution, the degree of the progress of the color-fading reaction is measured as a change in absorbance or transmittance, measuring time is preferably from 30 seconds to 60 minutes and more preferably from 5 to 30 minutes after the start of the color-fading reaction. During this period, it is necessary to measure it at least one time. In order to decrease the scattering in measurements, it is preferable to measure it two times or more.

In the present invention, an absorbance-measuring device is not limited if the device can measure absorbance within the range of 400–450 nm. A preferable measuring-device that can be used is, for example, a microtiter plate reader for wide uses, which is commonly used for ELISA etc., has good capability of being transported, and makes possible automatic continuous measurement and multi-specimen treatment.

Actually, the concentration of iodine in a specimen is measured as follows: a iodine standard solution having a known concentration, instead of the specimen, is used to measure its iodine concentration under the same conditions in advance or upon measurement of the specimen, thereby preparing a calibration curve about a relationship between absorbance or transmittance and iodine concentration, and then on the basis of this, the amount of iodine in the specimen is determined or detected. The iodine standard solution having a known concentration may be appropriately selected in accordance with the range concerning which the measurement is performed. In the case that the specimen is urine, it is necessary to select plural concentrations of at least two points between which a concentration 100 $\mu$g/L, which is an index of a normal value, is sandwiched.

Figure 1:
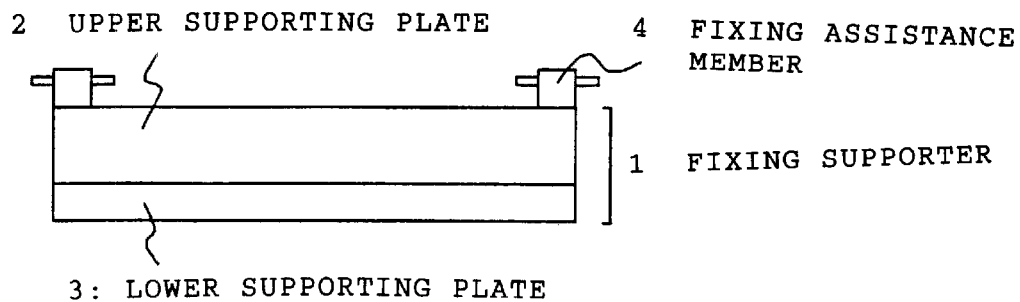
FIG. 1 is a view showing a front view of an example of an airtight tool, in use, for a microtiter plate.

EXPLANATION OF SYMBOLS 1 fixing supporter
2 upper supporting plate
3 lower supporting plate
4 fixing assistance member
5 reaction tool
6 spacer
7 spacer

BEST MODE FOR CARRYING OUT THE INVENTION

The present invention will be described by way of Examples.

EXAMPLE 1

Preparation of Reagents)
1) Chloric Acid Reagent Solution (20(W/V)%)

Five hundred grams of potassium chlorate were added to 900 ml of water and dissolved therein by heating. To the resultant solution were little by little (about 20 ml/minute) added 400 ml of 62 (W/V)% perchloric acid with stirring. The resultant aqueous solution was cooled with ice and then allowed to stand in a refrigerator (−20° C.) all night. Thereafter, the solution was filtered under reduced pressure to collect a filtrate. This was stored in the refrigerator until use thereof.

2) Arsenious Acid Reagent Solution

Twenty grams of arsenious acid were added to 500 ml of water, and then 14 g of sodium hydroxide were added thereto and dissolved therein. Further, 64 ml of concentrated sulfuric acid were added thereto, and then 50 g of sodium chloride were added thereto. Thereafter, water was added thereto so as to make a final solution volume up to 2 L. This was stored at room temperature until use thereof in the state that light was blocked off.

3) Ammonium Cerium Sulfate Reagent Solution

To 3.5 N sulfuric acid were dissolved 24.0 g of ammonium cerium sulfate dihydrate, so as to make a final solution volume up to 1 liter. This was stored at room temperature in the state that light was blocked off.

4) Iodine Standard Stock Solution 10 μg/ml

To water were dissolved 168 mg of potassium iodate (iodine: 100 mg), so as to make a final solution volume up to 100 ml (iodine: 1 mg/ml). One milliliter of this solution was taken off and diluted to 100 ml, so as to prepare a 10 μg/ml standard stock solution. This was stored at room temperature until use thereof.

1. Pretreatment of Specimens

As a reaction tool for pretreating specimens, there was used a 96-well microtiter plate (made by Corning Costar Japan) (hereinafter abbreviated to a plate A), made of polypropylene, in which 96 reaction areas (i.e., wells) were connected. Into the first and second rows, each of which was composed of 8 wells, i.e., 16 wells in total were put 40 μl of each of 0, 25, 50, 75, 100, 200, 300, and 400 ng/ml iodine standard solutions in such a manner that 2 wells were used for each of the concentrations. Into each of the wells were put 40 μl of each of 20 infant urine specimens in a iodine-deficiency region and 40 μl of each iodine-added urine prepared by adding 100 μl of each of an aqueous potassium iodate solution, containing 50 ng as an amount converted to iodine, to 1 ml of each of the urine specimens.

Next, 100 μl of the chloric acid reagent solution were respectively added to the wells of the plate A.

Figure 2:
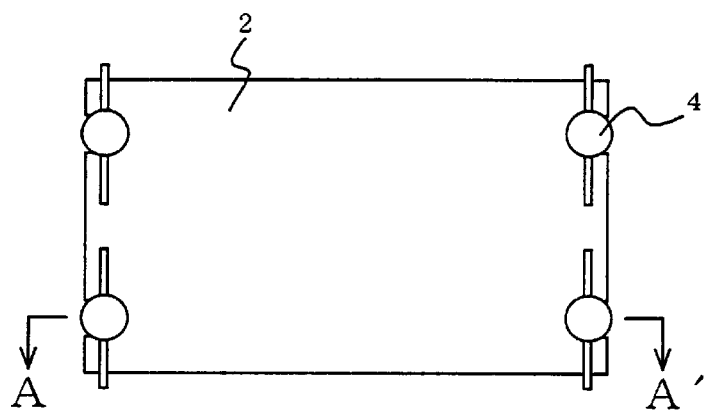
FIG. 2 is a view showing a plan view of the example of the airtight tool, in use, for the microtiter plate.
Figure 3:
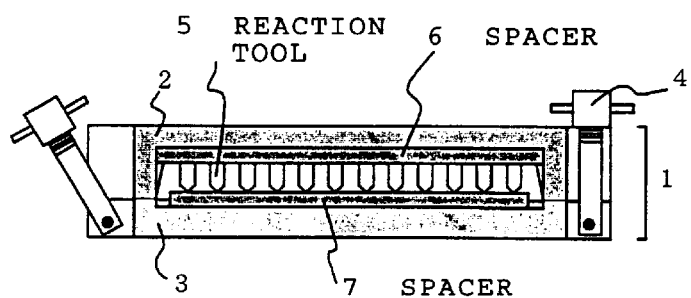
FIG. 3 is a view showing a sectional view (in the state that any snap screw as one fixing assistance member is taken off) taken on line a–a'.

Furthermore, in order to make the respective wells of the plate into an airtight state, the tool shown in FIGS. 1–3 was used as an airtight tool for the reaction tool of the 96-well mictotiter plate. Specifically, as the upper supporting plate 2 a supporter made of aluminum and having a size (length 200 mm×width 108 mm×height 30 mm) was used, as the lower supporting plate 3 a supporter made of aluminum and having a size (length 200 mm×width 108 mm×height 15 mm) was used, as the fixing assistance members 4 snap screws made of aluminum were used, as the spacer 6 a cover-like elastic silicone rubber plate (length 113 mm×width 81 mm×height 3 mm) which was an elastic body and covered with a polyvinylidene chloride film was used, and as the spacer 7 a cover-like elastic silicone rubber plate (length 108 mm×width 75 mm×height 3 mm) which was an elastic body and covered with a polyvinylidene chloride film was used. The size of a receiving space made when the upper supporting plate 2 and the lower supporting plate 3 were combined was a size of length 108 mm×width 90 mm×height 18 mm. A concave portion was made in each of the lower side of the upper supporting plate 2 and the upper side of the lower supporting plate 3, so that this receiving space would be made (the upper supporting plate: length 108 mm×width 90 mm×height 16 mm, and the lower supporting plate: length 108 mm×width 90 mm×height 2 mm).

The plate A (the reaction tool 5) was sandwiched between the two elastic bodies of the spacers 6 and 7, and was received in the state that the openings of the wells of the plate A were directed upward. Furthermore, by fastening the lower supporting plate 3 and the upper supporting plate 2 from the upper and lower sides by means of the fixing assistance members 4 fitted to the lower supporting plate 3, the respective wells of the plate A (the reaction tool 5) adhered closely and were made in an airtight state by means of the upper spacer 6 having elasticity. This was put inside a thermostat and heated at 105° C. for 1 hour. After the heating, the airtight tool for the mictotiter plate was taken out from the thermostat and then put on a heat-radiating plate. This was radiationally cooled up to room temperature and then the plate A (the reaction tool 5) was taken out.

2. Reaction (Sandell-Kolthoff Reaction) of the Reagent Solutions and Measurement of Absorbance After checking the return of the temperature of the plate A after the pretreatment of the specimens to room temperature, 40 μl were transferred with a multipipette from the reaction solution on this plate to a new 96-well mictotiter plate (made by Nalge Nunc International Co., Ltd.) (hereinafter abbreviated to a plate B) made of polystyrene. Next, 150 μl of the arsenious acid solution were added to all of the wells of the plate B. Using a 12-series multipipette, 40 μl of the ammonium cerium sulfate reagent solution were rapidly (within one minute) added to all of the wells. After 20 minutes, the plate B was set up to a microtiter plate reader (made by Tosoh Corp.) and then their absorbances were measured at a wavelength of 405 nm.

Figure 4:
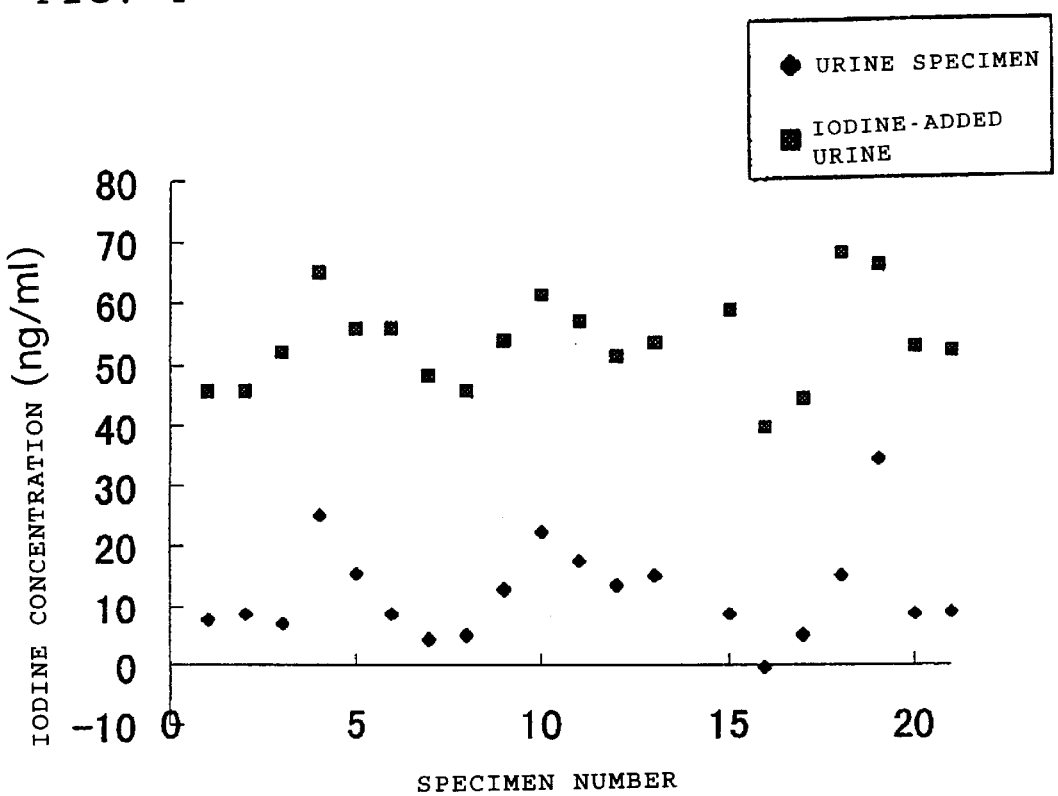
FIG. 4 is a graph showing results of a iodine addition recovery test in Example 1.

A calibration curve in which its horizontal axis expresses the concentration and its vertical axis expresses logarithm of the absorbance showed a straight line having a correlation coefficient of 0.99 or more. This fact suggests that interference materials having an influence on measured values were not eluted out from the vessel by the pretreatment. FIG. 4 shows plotted results of the measurement of the respective human urine specimens in the iodine-deficiency region and the urine specimens to which iodine was added, that is, plotted results of the addition recovery test. Each of the specimens showed a concentration of not more than 100 ng/ml, which was a normal value. Since iodine added in the iodine-added urines was quantitatively recovered, it was demonstrated that urine specimens of iodine-deficiency testees can be measured. The reliability of the measuring method of the present invention was demonstrated.

EXAMPLE 2

Preparation of Reagent Solutions

They were prepared according to Example 1.

1. Pretreatment of Specimens

As a reaction tool for pretreating specimens, there were used five 8-series tubes (made by Assist Co., Ltd.) made of polypropylene. Into the tubes (reaction areas) were put 10 μl of each of 0, 25, 50, 75, 100, 200, 300, and 400 ng/ml iodine standard solutions, 10 μl of each of 5 human urine specimens, and 10 μl of each of iodine-added urine specimens (prepared by adding 10 μl of an aqueous potassium iodate solution, containing 50 ng as an amount converted to iodine, to 1 ml of each of the urine specimens) in such a manner that the standard solution having each of the concentrations or each specimen was put into the two tubes. Into each of the tubes were put 100 μl of the chloric acid solution, and then the tubes were shut with 8-series caps (made by Assist Co., Ltd.) which were for PCR tubes and were made of polypropylene, as lids for making airtight, so as to make the tubes in an airtight state. Thereafter, this was put inside a thermostat and heated at 105° C. for 1 hour, and was then radiationally cooled up to room temperature.

2. Reaction (Sandell-Kolthoff Reaction) of the Reagent Solutions and Measurement of Absorbance To each treated solution after the pretreatment were added 150 μl of the arsenious acid solution, and then 100 μl were transferred from the solution to a new 96-well mictotiter plate made of polystyrene with a multipipette. Furthermore, with the multipipette, 40 μl of the ammonium cerium sulfate reagent solution were added thereto. After 30 minutes, the 96-well mictotiter plate made of polystyrene (made Nuljennunc International Co., Ltd., polystyrene) was set up to a microtiter plate reader (made by Tosoh Corp.) and then its absorbance was measured at a wavelength of 405 nm.

Table 1 shows average measured values (n=2) of the respective urine specimens and iodine-added urine specimens, and the results of recovery ratios by the addition of iodine. In the iodine-added urines, the respective specimens showed good recovery ratios of 93 to 103%. It was demonstrated that even if pretreatment is performed using the 8-series PCR tube made of polypropylene as connecting reaction areas under an airtight condition in which the tube is merely covered with the cap, interference materials can be removed.

TABLE 1

| Specimen No. | Average iodine concentration (ng/ml) | | Recovery ratio (%) |
| --- | --- | --- | --- |
| | Urine specimen | Iodine-added urine specimen | |
| 1 | 50.7 | 98.4 | 98 |
| 2 | 20.8 | 65.8 | 93 |
| 3 | 75.6 | 129.8 | 103 |
| 4 | 42.6 | 88.2 | 95 |
| 5 | 36.1 | 87.4 | 102 |

Average recovery ratio 98

EXAMPLE 3

Preparation of Reagent Solutions

They were prepared according to Example 1.

1. Step of Pretreating Specimens

As a reaction tool for pretreating specimens, there were used 8-series wells (NucleoLInk strip, made by Nalge Nunc International Co., Ltd.), for PCR, made of polycarbonate. They were fixed by means of a frame (made by Nuljennunc International Co., Ltd., Catalogue No. 249182), made of ABS (acrylonitrile-butadine-styrne), onto which 12 wells can hang. Into two wells was put each of 0, 5, 10, 25, 50, 100, 150, 200, 250, 300, 400 and 600 ng/ml iodine standard solutions. Moreover, 10 μl of each of 6 human urine specimens were respectively put into each of 6 wells (reaction areas), and 10 μl of each of iodine-added urine specimens thereof (prepared by adding 10 μl of an aqueous potassium iodate solution, containing 50 ng as an amount converted to iodine, to 1 ml of each of the urine specimens) were put into each of 6 wells. To all of these wells were added 100 μl of the chloric acid solution. In order to make the wells into an airtight state, they were covered with the silicone rubber plate 5, and then were sandwiched between two stainless supporting plates (thickness: 3 mm, width: 100 mm and length: 150 mm) as faxing supporters from the upper and lower sides, to make the wells airtight by screws as fixing assistance members. Thereafter, this was put inside a thermostat and heated at 105° C. for 60 minutes. Thereafter, this was radiationally cooled up to room temperature.

2. Reaction (Sandell-Kolthoff Reaction) of the Reagent Solutions and Measurement of Absorbance The same way as in Example 2 was performed.

Table 2 shows average measured values (n=6) of the respective urine specimens and iodine-added urine specimens, and the results of recovery ratios by the addition of iodine. In the iodine-added urines, the respective specimens showed good recovery ratios of 83 to 102%. Interference materials were completely removed by the pretreatment, and the vessel itself was colored into yellow with the oxidizing agent. It was not however observed that the interference materials were eluted out from the vessel. Thus, it was demonstrated that even if the polycarbonate vessel is used, the pretreatment can be attained.

TABLE 2

| Specimen No. | Average iodine concentration (ng/ml) | | Recovery ratio (%) |
| --- | --- | --- | --- |
| | Urine specimen | Iodine-added urine specimen | |
| 1 | 70.1 | 115.9 | 92 |
| 2 | 37.1 | 82.5 | 91 |
| 3 | 98 | 148.8 | 102 |
| 4 | 61.8 | 103.4 | 83 |
| 5 | 12.7 | 59.9 | 94 |
| 6 | 52.2 | 97.9 | 91 |

Average recovery ratio 92

EXAMPLE 4

Preparation of Reagent Solutions

They were prepared according to Example 1 except that the chloric acid reagent solution, which was a pretreating oxidizing agent, was changed into the following ammonium persulfate.

1) Ammonium Persulfate Reagent Solution

Into water were dissolved 200 g of ammonium persulfate, so as to make a final solution volume up to 1 liter.

1. Pretreatment of Specimens

Into two wells of a 96-microtiter plate (a plate A) made of polypropylene, as a reaction tool for pretreating specimens, was put each of 0, 5, 10, 25, 50, 100, 150, 200, 250, 300, 400 and 600 ng/ml iodine standard solutions, and into three wells thereof were put 10 μl of each of 12 human urine specimens and 12 iodine-added urine specimens (prepared by adding 10 μl of an aqueous potassium iodate solution, containing 50 ng as an amount converted to iodine, to 1 ml of each of the urine specimens). Furthermore, 50 µl of the ammonium persulfate reagent solution were added to all of the wells of the plate.

Using the airtight tool for the reaction tool used in Example 1, the plate A was made airtight in the same manner. Thereafter, the plate A was put inside a thermostat and heated at 105° C. for 1 hour. Subsequently, the airtight tool for the microplate was take out from the thermostat, and was put on a heat-radiating plate to cool it radiationally to room temperature. The plate A was then taken out.

2. Reaction (Sandell-Kolthoff Reaction) of the Reagent Solutions and Measurement of Absorbance The same way as in Example 2 was performed except that the reaction time after the addition of the ammonium cerium sulfate reagent solution was set up to 60 minutes.

The reaction rate of Sandell-Kolthoff reaction became somewhat slow, as compared with the case in which the pretreatment was conducted with chloric acid, and one hour, which was a substantially double time, was required for the reaction.

Table 3 shows average measured values (n=2) of the respective urine specimens and iodine-added urine specimens, and the results of recovery ratios by the addition of iodine. In the iodine-added urines, the respective specimens showed good recovery ratios of 87 to 116%. Interference materials were completely removed by the pretreatment and it was demonstrated that the interference materials are completely removed even by the pretreatment with ammonium persulfate.

TABLE 3

| Specimen No. | Average iodine concentration (ng/ml) | | Recovery ratio (%) |
|---|---|---|---|
| | Urine specimen | Iodine-added urine specimen | |
| 1 | 72.4 | 117.3 | 90 |
| 2 | 251 | 308.8 | 116 |
| 3 | 104.5 | 148.6 | 88 |
| 4 | 221.4 | 269.3 | 96 |
| 5 | 28 | 73.2 | 90 |
| 6 | 229.1 | 280.7 | 103 |
| 7 | 42.9 | 88.7 | 92 |
| 8 | 57.5 | 100.9 | 87 |
| 9 | 62.6 | 105.1 | 85 |
| 10 | 121.4 | 171.8 | 101 |
| 11 | 76.2 | 125.3 | 98 |
| 12 | 77.7 | 125.6 | 96 |

Average recovery ratio 95

COMPARATIVE EXAMPLE 1

A standard method in the prior art (Manual of measurement of iodine in urine, edited by International Council for Control of Iodine Deficiency Disorders, 1993)

Preparation of Reagent Solutions

They were prepared according to Example 1.

1. Pretreatment of Specimens

Twenty eight test tubes made of glass (inner diameter: 13 mm in length: 10 cm) were used. Into the test tubes were put 250 µl of each of 0, 25, 50, 75, 100, 200, 300, and 400 ng/ml iodine standard solutions, and each of 20 human urine specimens in such a manner that the standard solution having each of the concentrations or each specimen was put into the two tubes. Next, into all the tubes were put 750 µl of the chloric acid solution.

The test tubes were inserted into holes made in an aluminum block thermostat (Iwaki Glass Co., Ltd.) that was beforehand adjusted to 115° C. inside a locally-exhausting provision having an exhaust device, and was then heated for 1 hour. Thereafter, the test tubes were taken out from the thermostat and radiationally cooled.

2. Reaction (Sandell-Kolthoff Reaction) of the Reagent Solutions and Measurement of Absorbance After checking the return of the temperature of the test tubes after the pretreatment of the specimens nearly to room temperature, 3.5 ml of the arsenious acid solution were added to these test tubes. Next, 350 µl of the ammonium cerium sulfate reagent solution were added to the first test tube, and then the solution was rapidly stirred. The ammonium cerium sulfate reagent solution was added to the remaining test tubes at intervals of 20 seconds, using a stopwatch. Just after 20 minutes the addition of the ammonium cerium sulfate reagent solution, absorbance was measured at a wavelength of 405 nm.

Figure 5:
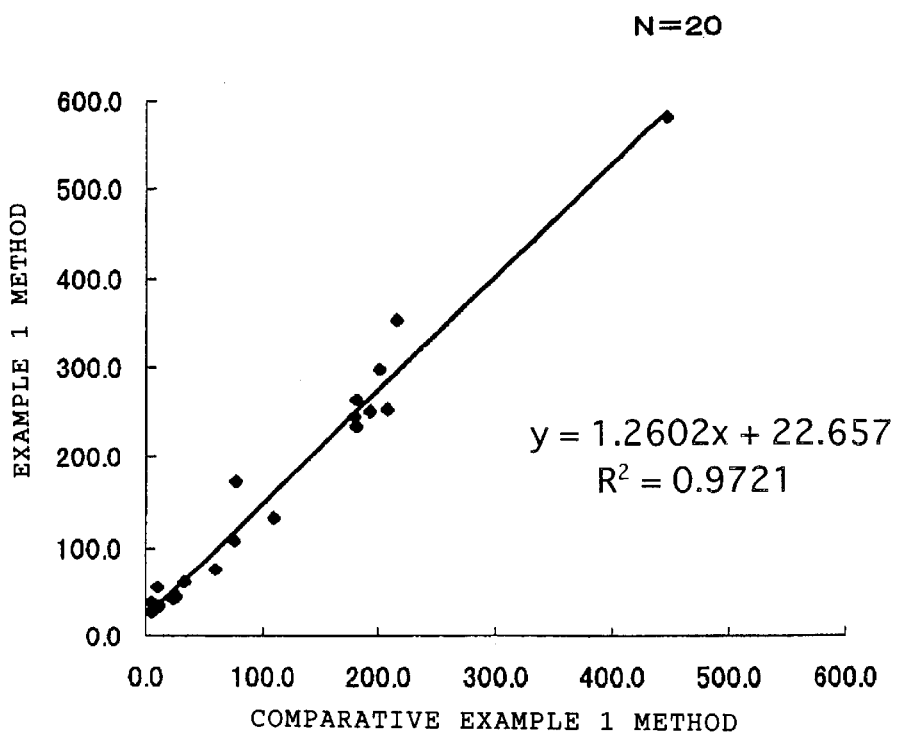
FIG. 5 is a graph showing a correlation between measured values of 20 urine specimens in Comparative Example 1 and measured results of the same specimens measured by the method of Example 1.

FIG. 5 shows a correlation graph between measured values of the 2 µl urine specimens in Comparative Example 1 and measurement results of the specimens of Comparative Example 1 which were measured according to Example 1. As a result, a good correlation was recognized.

However, it was recognized that vapor having an irritant smell peculiar to the oxidizing agent was generated from the test tubes by the pretreatment heating. About 4 ml of harmful wastes such as arsenic and the oxidizing agent were discharged per specimen. Furthermore, a change in the solution amount was measured so that about 0.5 g per tube was evaporated by the heating. Thus, an accidental error based on the change in the solution amount could not be ignored.

EXAMPLE 5

Preparation of Reagent Solutions

They were prepared according to Example 1.

1. Pretreatment of Specimens

As a reaction tool for pretreating specimens, there was used a 96-well microtiter plate (made by Coring Coaster Japan) made of polypropylene. Into 16 wells in total of the first and second rows were put 40 µl of each of 0, 25, 50, 75, 100, 200, 300, and 400 ng/ml iodine standard solutions in such a manner that 2 wells were used for each of the concentrations. Eighty human urine specimens were put into the other wells. Next, 100 µl of the ammonium persulfate reagent solution were added to all of the wells of the plate. Its weight was measured.

Using the airtight tool for the reaction tool used in Example 1, the microtiter plate was made airtight in the same manner. Thereafter, the airtight tool to which the microtiter plate was fitted was put inside a thermostat and heated at 105° C. for 1 hour. Subsequently, this was taken out from the thermostat, and was put on a heat-radiating plate to cool it radiationally to room temperature. The microtiter plate was then taken out and its weight was again measured.

2. Reaction (Sandell-Kolthoff Reaction) of the Reagent Solutions and Measurement of Absorbance The same way as in Example 2 was performed.

Figure 6:
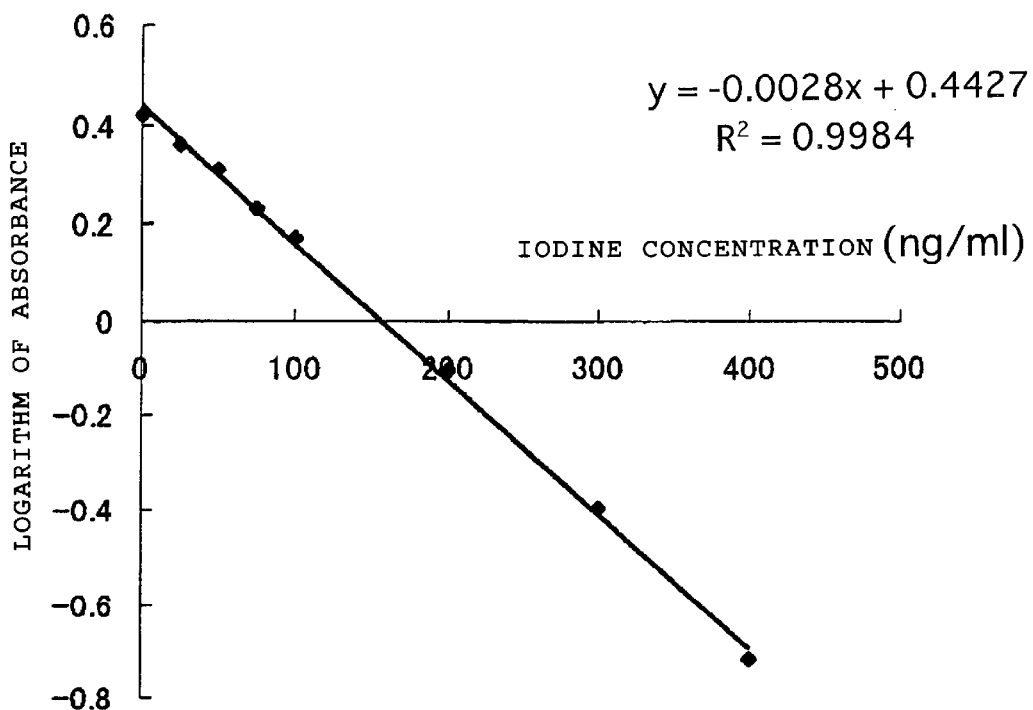
FIG. 6 is a graph showing a calibration curve of a relationship between iodine concentration and absorbance in Example 5.

As a result thereof, the weight of the plate pretreated using the airtight tool, for the reaction tool, for attaining an airtight condition was reduced by 0.3 g. A calibration curve of a relationship between absorbance and the iodine concentration is shown in FIG. 6.

COMPARATIVE EXAMPLE 2

The same way as in Example 5 was performed under the same conditions as therein except that in the pretreating reaction in Example 5 the airtight tool for the reaction tool was not used and the present system was made up to an open system and put inside a thermostat to perform pretreatment.

Figure 7:
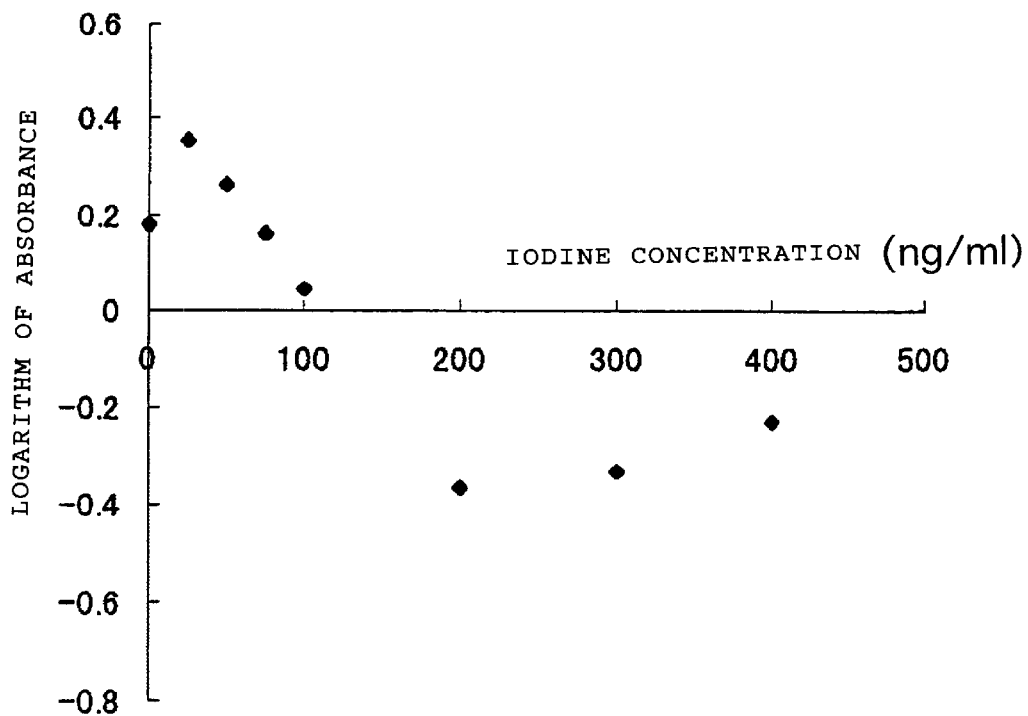
FIG. 7 is a graph showing a relationship between iodine concentration and absorbance in Comparative Example 2.

As a result thereof, the weight of the plate pretreated in the open system was reduced by about 9.2 g. Moreover, the solution amounts of the respective wells were scattered. It was recognized that vapor having an irritant smell peculiar to the oxidizing agent was generated by the pretreatment heating. In the case that the weight reduction was converted to a solution volume (the specific weight of the solution: 1) evaporated and scattered per well, 96 μl were on average evaporated and scattered. In two wells in the plate pretreated in the open system, crystal precipitated by evaporation and scatter of the solution. This would be because the pretreatment was performed in the open system so that difference in degrees of the evaporation was caused between the respective wells by temperature deviation of the plate and further be because the solution was scattered when bubbles of oxygen generated by decomposition of ammonium persulfate were burst. A relationship between absorbance and the iodine concentration is shown in FIG. 7. As shown in this graph, a one-to-one relationship was not obtained between the iodine concentration and the absorbance. Thus, quantitative analysis was impossible.

EXAMPLE 6

Preparation of Reagent Solutions

They were prepared according to Example 1.

1. Pretreatment of Specimens

The very same way as in Example 2 was performed except the following. There were used 4 human urine specimens, and iodine-added urine specimens wherein 50 ng/ml of iodine were added to the respective specimens (prepared by adding 10 μl of an aqueous potassium iodate solution, containing 50 ng as an amount converted to iodine, to 1 ml of each of the urine specimens) Heating operation in the step of pretreating the specimens was performed in an airtight state, and heating time was changed in the manner that heating was performed at 105° C. for 0.5 hour and 1.0 hour in the thermostat.

2. Reaction (Sandell-Kolthoff Reaction) of the Reagent Solutions and Measurement of Absorbance The very same way as in Example 2 was performed.

Table 4 shows average measured values (n=2) of the respective urine specimens and iodine-added urine specimens, and the results of recovery ratios by the addition of iodine. In the iodine-added urines, the respective specimens showed good recovery ratios of 94 to 108%. The average measured values (n=2) of the respective urine specimens and iodine-added urine specimens demonstrated that interference materials are removed by the pretreatment.

COMPARATIVE EXAMPLE 3

Preparation of Reagent Solutions

They were prepared according to Example 1.

1. Pretreatment of Specimens

The very same way as in Example 2 was performed except the following. There were used 4 human urine specimens, and iodine-added urine specimens wherein 50 ng/ml of iodine were added to the respective specimens (prepared by adding 10 μl of an aqueous potassium iodate solution, containing 50 ng as an amount converted to iodine, to 1 ml of each of theurine specimens). The heating operation after the attainment of the airtight state in the pretreatment of the specimens was omitted.

2. Reaction (Sandell-Kolthoff Reaction) of the Reagent Solutions and Measurement of Absorbance The very same way as in Example 2 was performed.

Table 4 shows average measured values (n=2) of the respective urine specimens and iodine-added urine specimens, and the results of recovery ratios by the addition of iodine. That is, the recovery ratio in the case in which chloric acid was added and no heating operation was performed was compared with the recovery ratios in the cases in which heating was performed at 105° C. for 30 minutes and 1 hour. Table 4 shows that in the case in which no heating operation was performed, the addition recovery ratio of iodine was on average only 58% while the average recovery ratios by the 0.5 hour 30-minute-heating and the 1-hour-heating in Example 5 were 97% and 101%, respectively.

TABLE 4

| Specimen No. | Comparative Example 3 | Example 6 | |
|---|---|---|---|
| | 0 hour | 0.5 hour | 1 hour |
| 1 | 54 | 91 | 97 |
| 2 | 65 | 97 | 94 |
| 3 | 57 | 99 | 105 |
| 4 | 56 | 100 | 108 |
| Average recovery ratio | 58 | 97 | 101 |

EXAMPLE 7

Preparation of Reagent Solutions

They were prepared according to Example 1.

1. Pretreatment of Specimens

Into two wells of a 96-microtiter plate (a plate A) made of polypropylene, as a reaction tool for pretreating specimens, were put 10 μl of each of 0, 5, 10, 25, 50, 100, 150, 200, 250, 300, 400 and 600 ng/ml iodine standard solutions, and into four wells thereof were put 10 μl of each of 6 human urine specimens, and 10 μl of each of 6 iodine-added urine specimens (prepared by adding 10 μl of an aqueous potassium iodate solution, containing 50 ng as an amount converted to iodine, to 1 ml of each of the urine specimens) . To all of these wells were added 100 of the chloric acid solution. Subsequent pretreatment of the specimens was performed in the same way as in Example 1 except that the temperatures of the thermostat were set to 80° C., 100° C. and 120° C. and heating for 30 minutes was respectively conducted.

Reaction (Sandell-Kolthoff Reaction) of the Reagent Solutions and Measurement of Absorbance The very same way as in Example 3 was performed.

Figure 8:
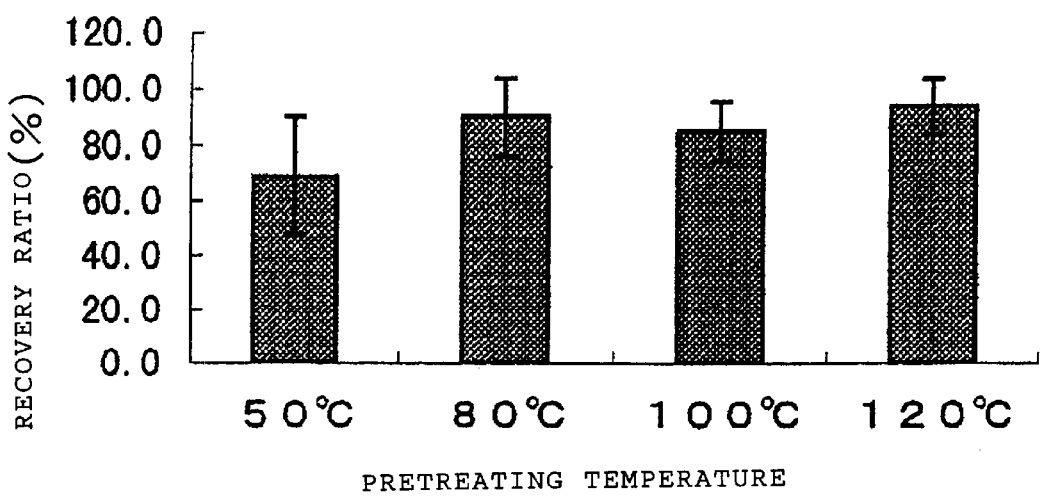
FIG. 8 is a graph showing a relationship between reaction temperature of pretreatment and iodine addition recovery ratio in Examples 7 and 8.

FIG. 8 shows a relationship between the reaction temperature of the pretreatment and the recovery ratio of measured values by the addition of iodine.

EXAMPLE 8

Preparation of Reagents

They were prepared according to Example 1.

1. The very same way as in Example 7 was performed except that the temperature of the thermostat was set to 50° C. and heating was conducted.

3. Reaction (Sandell-Kolthoff Reaction) of the Reagent Solutions and Measurement of Absorbance The very same way as in Example 3 was performed.

Using 12 human urine specimens, and iodine-added urine specimens in which 50 ng/ml of iodine were added to each of the specimens (prepared by adding 10 μl of an aqueous potassium iodate solution, containing 50 ng as an amount converted to iodine, to 1 ml of each of the urine specimens), pretreating temperature was set to 50° C. and the reaction was caused to advance for 30 minutes. The addition recovery ratio of iodine at this time was examined.

The reaction temperatures (heating temperatures) of the pretreatment were compared with the recovery ratios of measured values by the addition of iodine. A relationship between the addition recovery ratios of iodine in Examples 7 and 8 is shown in FIG. 8.

From these results, the recovery ratios in the case that the pretreating temperature was 50° C. in Example 8 were low on average and scattering was large between the specimens. It is presumed that the recovery ratios depend on the content of interference materials in the specimens. On the other hand, recovery ratios of 90% or more were obtained in the case that the pretreating temperature was 80° C. or higher in Example 7. From this result, it is preferred that the pretreating temperature for removing any interference material in urine is set within a range of 80–120° C. (both inclusive) rather than 50° C.

EXAMPLE 9

Preparation of Reagents

The same way as in Example 1 was performed except that concerning the concentration of chloric acid used in the heating pretreatment in the method described in Example 1, conditions thereof were changed. That is, to the chloric acid reagent solution used in the pretreatment (20 (W/V) %) was added purified water in an equivalent amount, so as to set the concentration of chloric acid up to 10 (W/V)%.

1. Pretreatment of Specimens

Using 5 human urine specimens, and 5 iodine-added urine specimens (prepared by adding 10 μl of an aqueous potassium iodate solution, containing 50 ng as an amount converted to iodine, to 1 ml of each of the urine specimens), the same way as in Example 2 was performed except that the 10 (W/V) % chloric acid was used in pretreatment.

2. Reaction (Sandell-Kolthoff Reaction) of the Reagent Solutions and Measurement of Absorbance The same way as in Example 2 was performed.

Results of the addition recovery ratios of iodine in the urines of Examples 2 and 9 are shown in Table 5. Scattering in the recovery ratios was large between the specimens in the case of the pretreatment with the 10% chloric acid in Example 9. Thus, effect of interference materials in the urines is presumed. On the other hand, recovery ratios of 90% or more were shown in the case of 20% chloric acid in Example 2. That is, it is preferred that the concentration of chloric acid to be added for pretreatment more rather than 10%.

TABLE 5

| Specimen No. | Example 9 10% chloric acid | Example 2 20% chloric acid |
|---|---|---|
| 1 | 88 | 98 |
| 2 | 60 | 93 |
| 3 | 106 | 103 |
| 4 | 85 | 95 |
| 5 | 64 | 102 |
| Average recovery ratio | 81 | 98 |

EXAMPLE 10

Preparation of Reagents

They were prepared according to Example 1.

1. Production of a Reaction Tool (a Plate A) for Pretreating Specimens

As a reaction tool for pretreating specimens, four 96-well microtiter plates (made by Coring Coaster Japan), made of polypropylene, were used. Into 22 wells of the respective plates were put 10 μl of 0, 25, 50, 75, 100, 150, 200, 250, 300, 400 and 600 ng/ml iodine standard solutions in the manner that each of the respective concentration solutions was put into 2 wells (the plate A).

2. Pretreatment of Specimens

Into each of the wells to which no iodine standard solution was added were put 283 human urine specimens whose measurement values were known by measurement through an autoanalyzer method (Technicon Instrument Company). Furthermore, 100 μl of the chloric acid solution were added to each of the iodine standard solutions and the human urine specimens.

The same way as in Example 1 was performed.

3. Reaction (Sandell-Kolthoff Reaction) of the Reagent Solutions and Measurement of Absorbance After checking the return of the temperature of the plate A after the pretreatment of the specimens nearly to room temperature, 150 μl of the arsenious solution were added to all wells of a plate B. 60 μl of the reaction solution in this plate A were transferred to a new 96-well microtiter plate (made by Nalge Nunc International Co., Ltd., polystyrene (the plate B) Using a 12-series multipipette, 40 μl of the ammonium cerium sulfate reagent solution were rapidly (within one minute) added to all of the wells. After 30 minutes, the plate B was set up to a microtiter plate reader (made by Tosoh Corp.) and then their absorbances were measured at a wavelength of 405 nm.

Figure 9:
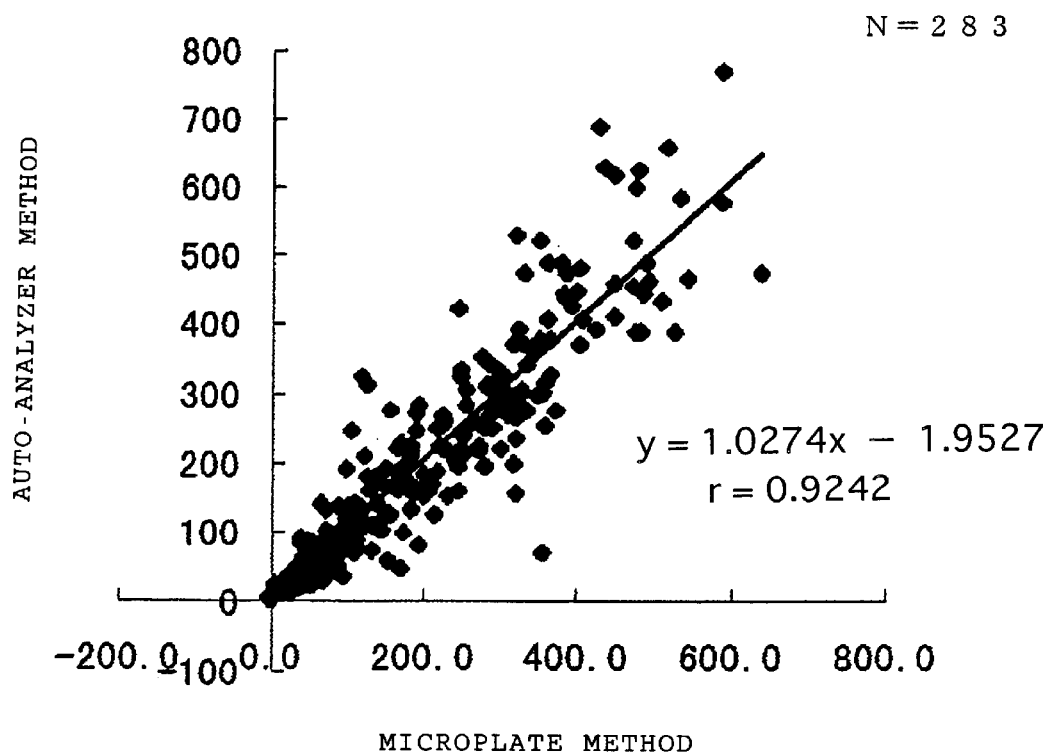
FIG. 9 is a graph showing a correlation between measured values of human urine specimens by the autoanalyzer method and those in Example 10.

A correlation between measured results of the 283 human urine specimens by the autoanalyzer method (Technicon Instrument Company) and those of Example 10 was examined, and a result thereof is shown in FIG. 9. The result showed a good correlation having a correlation coefficient of about 0.92 and an inclination of 1.03.

INDUSTRIAL APPLICABILITY

According to the method for measuring iodine as recited in claim 1, no special provision such as a locally-exhausting provision in pretreatment is required and it is possible to pretreat a specimen safely and obtain measured values with good reproducibility by suppressing scattering of harmful vapor and a change in the solution amount of a reaction solution.

According to the method for measuring iodine as recited in claim 2, it is possible to pretreat a specimen with safety and high reliability since there do not arise troubles such as damage of any vessel upon heating treatment.

According to the method for measuring iodine as recited in claim 3, no special provision such as a locally-exhausting provision in pretreatment is required and it is possible to pretreat a specimen with safety and high reliability and obtain measured values with good reproducibility by suppressing scattering of harmful vapor and a change in the solution amount of a reaction solution and by no occurrence of troubles such as damage of any vessel.

According to the method for measuring iodine as recited in claim 4, the same effects produced by the inventions of claims 2 or 3 are exhibited and it is possible to pretreat a great number of specimens promptly and easily. This method is suitable for measuring a great number of specimens.

According to the method for measuring iodine as recited in claim 5, the same effects produced by the inventions of claims 2–4 are exhibited and it is possible to pretreat a specimen with safety and high reliability by no occurrence of troubles such as damage of any vessel upon heating treatment and no outflow of such materials that have an effect on measured values.

According to the method for measuring iodine as recited in claim 6, the same effects produced by the inventions of claims 2–5 are exhibited and it is possible to obtain a low-priced and highly reliable reaction tool and pretreat safely a specimen without troubles such as damage of any vessel upon heating treatment nor outflow of such materials that have an effect on measured values.

According to the specimen-pretreating reaction tool as recited in claim 7, it is possible to pretreat safely a great number of specimens without troubles such as damage of any vessel upon heating treatment nor outflow of such materials that have an effect on measured values.

According to the airtight tool, for the specimen-pretreating reaction tool as recited in claim 8, no special provisions such as a locally-exhausting provision is required in pretreatment of specimens for measuring iodine. No limitations are imposed on places where specimens are treated and evaporation of harmful vapor and the generation amount of harmful waste can be suppressed. Besides, it is possible to pretreat a great number of specimens easily.

What is claimed is:

1. A iodine-measuring method for determining or detecting iodine concentration in a specimen, comprising a specimen-pretreating step of thermally digesting a specimen together with an oxidizing agent, wherein said sample is heated and then cools, and a subsequent reaction-measuring step of reacting the sample with an arsenious acid reagent solution and an ammonium cerium sulfate reagent solution and measuring absorbance in the reaction solution, wherein the specimen-pretreating step is performed under an airtight condition, using an airtight tool comprised of: (i) a specimen-pretreating reaction tool that is made of a heat-resistant and oxidation-resistant organic material and that provides reaction areas; and (ii) upper and lower fixing supporters that cover the reaction areas such that the lower fixing supporter cools earlier than the upper fixing supporter.

2. The iodine-measuring method according to claim 1, wherein the reaction tool made of the heat-resistant organic material is a tool having plural reaction areas.

3. The iodine-measuring method according to claim 1, wherein the heat-resistant organic material is a polypropylene resin, a polycarbonate resin, a polysulfone resin, a polyethersulfone resin, a Teflon resin, or a polymethylpentene resin.

4. The iodine-measuring method according to claim 1, wherein the reaction tool is a microtiter plate.

5. The iodine-measuring method according to claim 1, wherein the airtight tool is composed of said specimen-pretreating reaction tool, and two, upper and lower fixing supporters which can cover reaction areas of this specimen-pretreating reaction tool with a spacer sandwiched and fixed from upper and lower sides, and fixing assistance members capable of applying pressure to these fixing supporters so that the reaction areas of the reaction tool can be made airtight by aid of spacer.

6. The iodine-measuring method according to claim 5, wherein the upper fixing supporter is made thicker than the lower fixing supporter.

7. The iodine-measuring method according to claim 5, wherein the cooling treatment is performed in such a manner that the lower fixing supporter is forcibly brought into contact with water or a heat-radiating plate.

* * * * *